United States Patent
Samarage et al.

(10) Patent No.: US 12,102,414 B2
(45) Date of Patent: Oct. 1, 2024

(54) METHOD OF SCANNING AND ASSESSING LUNG AND VASCULAR HEALTH

(71) Applicants: 4DMedical Limited, Melbourne (AU); Cedars-Sinai Medical Center, Los Angeles, CA (US)

(72) Inventors: Chaminda Rajeev Samarage, Melbourne (AU); Andreas Fouras, Woodland Hills, CA (US); Heather Jones, Malibu (CA); Victor Tapson, Studio City, CA (US)

(73) Assignees: 4DMedical Limited, Melbourne (AU); Cedars-Sinai Medical Center, Los Angeles, CA (US)

( * ) Notice: Subject to any disclaimer, the term of this patent is extended or adjusted under 35 U.S.C. 154(b) by 840 days.

(21) Appl. No.: 16/489,334

(22) PCT Filed: Feb. 27, 2018

(86) PCT No.: PCT/AU2018/000028
§ 371 (c)(1),
(2) Date: Aug. 27, 2019

(87) PCT Pub. No.: WO2018/157191
PCT Pub. Date: Sep. 7, 2018

(65) Prior Publication Data
US 2020/0069197 A1    Mar. 5, 2020

Related U.S. Application Data

(60) Provisional application No. 62/464,540, filed on Feb. 28, 2017.

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0205* (2013.01); *A61B 5/1075* (2013.01);
(Continued)

(58) Field of Classification Search
CPC ... A61B 5/02007; A61B 5/0205; A61B 5/055; A61B 5/08; A61B 5/1075; A61B 5/489;
(Continued)

(56) References Cited

U.S. PATENT DOCUMENTS 5,491,642 A    2/1996   Wormell et al.
6,373,920 B1   4/2002   Hsieh
(Continued)

FOREIGN PATENT DOCUMENTS

DE    19948827 A1    4/2001
EP    2873371 A1     5/2015
(Continued)

OTHER PUBLICATIONS

Frangi et al. "Multiscale vessel enhancement filtering." Proc. 1998 MICCAI Int'l Conf. on Medical Image Computing and Computer-Assisted Intervention, Cambridge, Mass., 8 pp. (Oct. 11, 1998).
(Continued)

*Primary Examiner* — Alexei Bykhovski
(74) *Attorney, Agent, or Firm* — LOZA & LOZA, LLP; David S. Sarisky

(57) ABSTRACT

The invention relates to a method of scanning for vascular ill health using a data set from an in vivo scan, the method including the steps of: (1) extracting blood vessel location data and blood vessel size data from the scan data set; (2) selecting a region in the extracted vessel location data; and (3) comparing the size data in the selected region to size data in a corresponding region of a normative data set to determine vascular health.

28 Claims, 7 Drawing Sheets

(51) Int. Cl.
*A61B 5/0205* (2006.01)
*A61B 5/107* (2006.01)
*G16H 20/10* (2018.01)
*G16H 30/40* (2018.01)
*G16H 50/20* (2018.01)
*A61B 5/055* (2006.01)

(52) U.S. Cl.
CPC ............ *A61B 5/489* (2013.01); *G16H 20/10* (2018.01); *G16H 30/40* (2018.01); *G16H 50/20* (2018.01); *A61B 5/055* (2013.01)

(58) Field of Classification Search
CPC . G06T 2207/10081; G06T 2207/20021; G06T 2207/20076; G06T 2207/30101; G06T 7/0014; G16H 20/10; G16H 30/40; G16H 50/20
See application file for complete search history.

(56) References Cited

U.S. PATENT DOCUMENTS

| | | | |
|---|---|---|---|
| 6,385,332 | B1 | 5/2002 | Zahalka et al. |
| 6,549,646 | B1 | 4/2003 | Yeh et al. |
| 6,631,716 | B1 | 10/2003 | Robinson et al. |
| 6,650,928 | B1 | 11/2003 | Gailly et al. |
| 6,816,607 | B2 | 11/2004 | O'Donnell et al. |
| 7,333,643 | B2 | 2/2008 | Murphy et al. |
| 7,376,253 | B2 | 5/2008 | Spreeuwers et al. |
| 7,583,829 | B2 | 9/2009 | Kiraly et al. |
| 7,668,357 | B2 | 2/2010 | Keall et al. |
| 7,742,639 | B2 | 6/2010 | Eck et al. |
| 7,876,936 | B2 | 1/2011 | Raffy |
| 7,985,187 | B2 | 7/2011 | Wibowo et al. |
| 8,090,176 | B2 | 1/2012 | Kinnstaetter et al. |
| 8,175,358 | B2 | 5/2012 | Weese et al. |
| 8,346,342 | B2 | 1/2013 | Kalafut |
| 8,447,380 | B2 | 5/2013 | Kuth et al. |
| 8,483,456 | B2 | 7/2013 | Nagatsuka et al. |
| 8,538,111 | B2 | 9/2013 | Zhang et al. |
| 8,553,832 | B2 | 10/2013 | Camus et al. |
| 8,613,710 | B2 * | 12/2013 | Kolanko ............... A61B 5/0082 351/200 |
| 8,666,139 | B2 | 3/2014 | Zhang et al. |
| 8,668,652 | B2 | 3/2014 | Wibowo et al. |
| 8,878,838 | B2 | 11/2014 | Hautvast |
| 9,025,849 | B2 | 5/2015 | Fouras et al. |
| 9,036,887 | B2 | 5/2015 | Fouras et al. |
| 9,044,194 | B2 | 6/2015 | Noji et al. |
| 9,125,621 | B2 | 9/2015 | Nagatsuka et al. |
| 9,198,628 | B2 | 12/2015 | Shimada et al. |
| 9,254,112 | B2 | 2/2016 | Tryggestad et al. |
| 9,289,140 | B2 | 3/2016 | Ross et al. |
| 9,311,702 | B2 | 4/2016 | Pautot |
| 9,760,989 | B2 | 9/2017 | Yin et al. |
| 9,892,513 | B2 | 2/2018 | Gurevich et al. |
| 9,962,086 | B2 | 5/2018 | Dabbah et al. |
| 9,999,401 | B2 | 6/2018 | Korporaal et al. |
| 10,282,841 | B1 * | 5/2019 | Parsons-Wingerter ..................... G06T 7/0014 |
| 2004/0092811 | A1 | 5/2004 | Hill |
| 2005/0053267 | A1 | 3/2005 | Mostafavi |
| 2005/0059876 | A1 | 3/2005 | Krishnan et al. |
| 2005/0113672 | A1 | 5/2005 | Salla |
| 2005/0187464 | A1 | 8/2005 | Ho et al. |
| 2005/0240094 | A1 | 10/2005 | Pinchon et al. |
| 2007/0092864 | A1 | 4/2007 | Reinhardt et al. |
| 2008/0031404 | A1 | 2/2008 | Khamene |
| 2008/0077038 | A1 | 3/2008 | McDonough |
| 2008/0181481 | A1 | 7/2008 | Hong et al. |
| 2008/0193904 | A1 | 8/2008 | Santhanam et al. |
| 2008/0269592 | A1 | 10/2008 | Kuth |
| 2009/0003511 | A1 * | 1/2009 | Roy ...................... A61B 5/415 378/4 |
| 2009/0207968 | A1 | 8/2009 | Grass |
| 2009/0208084 | A1 | 8/2009 | Liu et al. |
| 2009/0252394 | A1 | 10/2009 | Liang et al. |
| 2010/0041992 | A1 | 2/2010 | Ohuchi et al. |
| 2010/0063410 | A1 | 3/2010 | Avila |
| 2010/0191131 | A1 | 7/2010 | Revishvili et al. |
| 2010/0222671 | A1 * | 9/2010 | Cohen ...................... G06T 5/00 600/424 |
| 2010/0228143 | A1 | 9/2010 | Teschner |
| 2011/0051885 | A1 | 3/2011 | Buelow et al. |
| 2012/0041318 | A1 | 2/2012 | Taylor |
| 2013/0046176 | A1 | 2/2013 | Mistretta et al. |
| 2013/0070062 | A1 | 3/2013 | Fouras et al. |
| 2014/0192952 | A1 | 7/2014 | Keall et al. |
| 2015/0320325 | A1 * | 11/2015 | Sheehan ............... A61B 8/4416 600/475 |
| 2016/0095580 | A1 | 5/2016 | Rubin |
| 2016/0220129 | A1 * | 8/2016 | Ostroverkhov ....... A61B 5/0261 |
| 2017/0309016 | A1 * | 10/2017 | Klaiman ................... G06T 7/73 |

FOREIGN PATENT DOCUMENTS

| | | |
|---|---|---|
| EP | 2299286 B1 | 9/2020 |
| JP | 2007089674 A | 4/2007 |
| JP | 2010046212 A | 3/2010 |
| KR | 10-2004-006584 A | 7/2004 |
| WO | 2006116178 A1 | 11/2006 |
| WO | 2008085048 A1 | 7/2008 |
| WO | 2011017739 A1 | 2/2011 |
| WO | 2011032210 A1 | 3/2011 |
| WO | 2012026145 A1 | 3/2012 |
| WO | 2013053000 A1 | 4/2013 |
| WO | 2013155556 A1 | 10/2013 |
| WO | 2014143974 A1 | 9/2014 |
| WO | 2015157799 A1 | 10/2015 |

OTHER PUBLICATIONS

Jimenez-Carretero et al. 3D frangi-based lung vessel enhancement filter penalizing airways. Proc. 2013 IEEE 10th International Symposium on Biomedical Imaging, San Francisco, CA, 4 pages (Apr. 7, 2013).

Qian et al. "A non-parametric vessel detection method for complex vascular structures." Medical Image Analysis, vol. 13, Issue 1, pp. 49-61 (Feb. 2009).

Rudyanto et al. "Quantification of pulmonary vessel diameter in low-dose CT images." Proceedings vol. 414 Medical Imaging 2015, Computer-Aided Diagnosis Orlando, Florida, 6 pages (Feb. 21, 2015).

Sato et al. "TEASAR: Tree-structure extraction algorithm for accurate and robust skeletons." Proc. 8th Pacific Conf. on Computer Graphics and Applications, Hong Kong, China, pp. 281-449 (2000).

Schindelin et al. "Fiji -an Open Source platform for biological image analysis." Nature Methods, vol. 9, No. 7 15 pp. (Jun. 28, 2012).

Soria et al. "Accuracy of out-of-plane vorticity component measurement using in-plane velocity vector field measurements." 12th Australasian Conference on Fluid Mechanics, Univ. Sydney, Australia (Dec. 10, 1995).

Staring et al. "Pulmonary vessel segmentation using vessel enhancement filters." Grand Challenge Website, available online at https://grand-challenge.org/site/VESSEL 12/Results/ insertresults/ public/20120328103241_163_LKEBChina_ VESSEL 12_StrainEnergy/algorithm_description.pdf (Jan. 2012).

Sun et al. "Detection of central pulmonary embolism on non-contrast .computed tomography: a case control study." Int'l J. Cardiovascular Imaging, vol. 30, No. 3, 8 pages (Mar. 2014).

Wittram et al. "CT Angiography of Pulmonary Embolism: Diagnostic Criteria and Causes of Misdiagnosis." RadioGraphics vol. 24, No. 5, 20 pp., (Sep. 1, 2004).

PCT/AU2017/000054. Int'l Search Report (Jun. 22, 2017).

Barker et al. "3-Component Phase-Contrast MRI WSS Vectors in the Carotid Bifurcation are Concurrent with Local Atherosclerotic Plaque Risk Hypotheses.", Proc. Intl. Soc. Mag. Reson. Med. 18 (2010).

(56) References Cited

OTHER PUBLICATIONS

Brahme et al. "4D laser camera for accurate patient positioning, collision avoidance, image fusion and adaptive approaches during diagnostic and therapeutic procedures.", Int'l J. Physics Research & Practice. vol 35:5 (May 2008).

Choi et al. "Numerical study of high-frequency oscillatory air flow and convective mixing in a CT-based human airway model.", Annals Biomed. Engr. vol. 38:12, pp. 3550-3571 (Dec. 2010).

Christensen et al., "Tracking lung tissue motion and expansion/compression with inverse consistent image registration and spirometry.", Int'l J. Med. Phys. Res.And Practice, vol. 34:6, Part 1 (first published May 21, 2007).

Cui et al., "Fluoroscopic gating without implanted fiducial markers for lung cancer radiotherapy based on support vector machines.", Phys Med Biol, 53:N315-27 (2008).

Docef et al. "Deformed CT reconstruction from limited projection data.", Int'l. Congress Series, vol. 1281, pp. 104-108 (May 2005).

Dubsky et al. "Three component, three dimensional X-ray particle image velocimetry using multiple projections.", 14th Int Symp on Applications of Laser Techniques to Fluid Mechanics, Lisbon, Portugal (Jul. 7-10, 2008).

Dubsky et al. "Computed tomographic x-ray velocimetry for simultaneous 3D measurement of velocity and geometry in opaque vessels.", Experiments In Fluids vol. 52:3 pp. 543-554 (Mar. 2012).

Dubsky et al. "Synchrotron-based dynamic computed tomography of tissue motion for regional lung function measurement.", J. Royal Soc. Interface https://doi.org/10.1098/rsif.2012.0116 (Apr. 4, 2012).

Fouras et al. "Three-dimensional synchrotron x-ray particle image velocimetry", J. Applied Physics 102 064916 (Sep. 28, 2007).

Fouras, et al. "The past, present, and future of x-ray technology for in vivo imaging of function and form.", J. Applied Physics. 105, 102009 (2009).

Fouras et al. "In-vivo Synchrotron PIV for the measurement of airway motion.", 8th Int'l Symposium on Particle Image Velocimetry-PIV09 Melbourne Victoria Australia (Aug. 25-28, 2009).

Fouras et al. "Engineering imaging: using particle image velocimetry to see physiology in a new light.", Clinical & Experi. Pharmacology and Physiology 36,238-247 (2009).

Guerrero et al. "Dynamic ventilation imaging from four-dimensional computed tomography.", Physics in Medicine & Biology, vol. 51:4 (Jan. 25, 2006).

Irvine, et al. "Phase retrieval for improved three-dimensional velocimetry of dynamic x-ray blood speckle.", Appl. Phys. Lett. 93, 153901 (Oct. 15, 2008).

Kim et al. "X-ray PIV measurements of blood flows without tracer particles.", Experiments in Fluids, vol. 41:2, pp. 195-200 (Aug. 2006).

Lu et al. "Blood flow velocity and ultra-filtration velocity measured by CT imaging system inside a densely bundled hollow fiber dialyzer.", Int'l J. of Heat and Mass Transfer. vol. 53:9-10, pp. 1844-1850 (Apr. 2010).

Rodriguez-Romero, et al. "The influence of respiratory motion on CT image volume definition.", Int. J. Med. Phys. Res. & Practice vol. 41:4 (Mar. 7, 2014).

Simon, "Regional ventilation and lung Mechanics Using X-Ray CT1.", Academic Radiology vol. 12:11, pp. 1414-1422 (Nov. 2005).

Soussen et al. "Polygonal and polyhedral contour reconstruction in computed tomography.", IEEE Transactions on Image Processing, vol. 13:11 (Nov. 2004).

Thurgood et al. "Functional lung imaging during HFV in preterm rabbits.", PLOS One; https://doi.org/10.1371/journal.pone.0048122 (Oct. 30, 2012).

Wiepütz et al. "Simultaneous Assessment of Airway Instability and Respiratory Dynamics with Low-Dose 4D-CT in Chronic Obstructive Pulmonary Disease: A Technical Note." Respiration 87:294-300 (2014).

Wong et al. "Cardiac flow component analysis.", Medical Engr. & Physics vol. 32:2 pp. 174-188 (Mar. 2010).

Yin et al., "Simulation of pulmonary air flow with a subject-specific boundary condition.", J. Biomechanics vol. 43:11, pp. 2159-2163 (Aug. 10, 2010).

Zhang et al. "Evaluation of segmentation algorithms for vessel wall detection in echo particle image velocimetry.", IEEE Int'l Ultrasonics Symposium (DOI: 10.1109/ULTSYM.2009.5441630) (Sep. 20, 2009).

PCT/AU2012/001225 Int'l Prelim. Report on Patentability (Apr. 15, 2014).

PCT/AU2015/000219 Int'l Search Report (Jun. 4, 2015).

PCT/AU2013000390. Int'l Prelim. Report on Patentability (Oct. 21, 2014).

Orkisz, M. et al.: "Segmentation of the Pulmonary Vascular Trees in 3D CT Images Using Variational Region-Growing", IRBM, vol. 35, 2014, pp. 11-19, XP055470067. (9 Pages).

International Search Report and Written Opinion of the International Searching Authority for PCT/AU2018/000028 dated Jun. 8, 2018. (17 Pages).

* cited by examiner

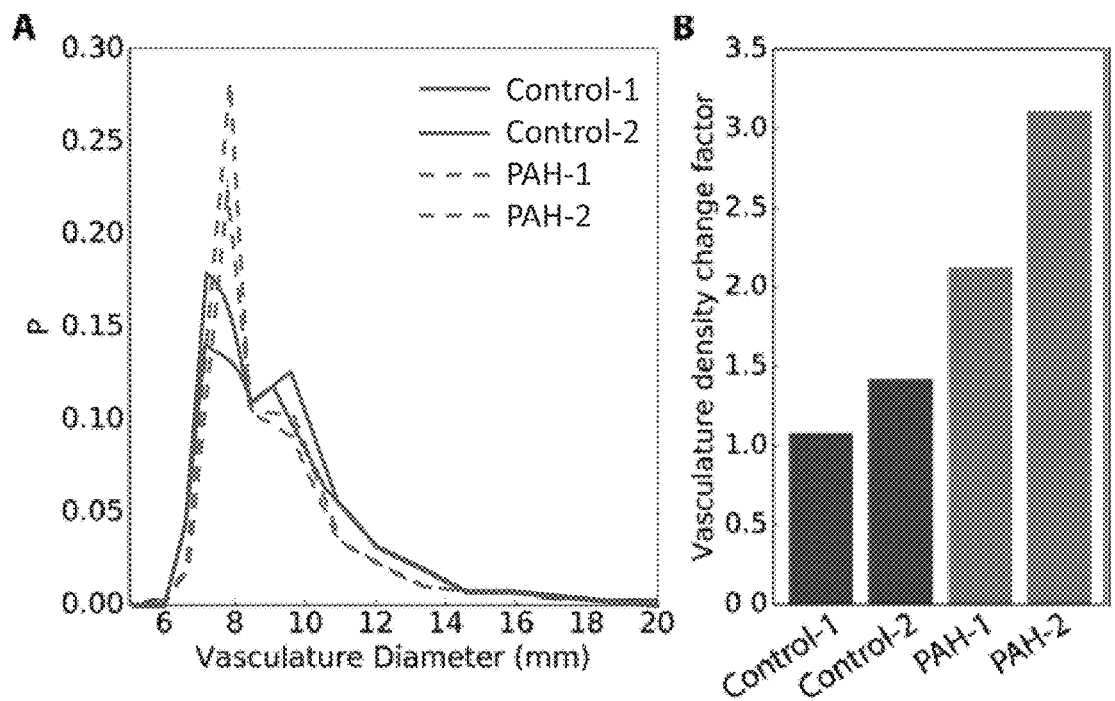
Figure 7
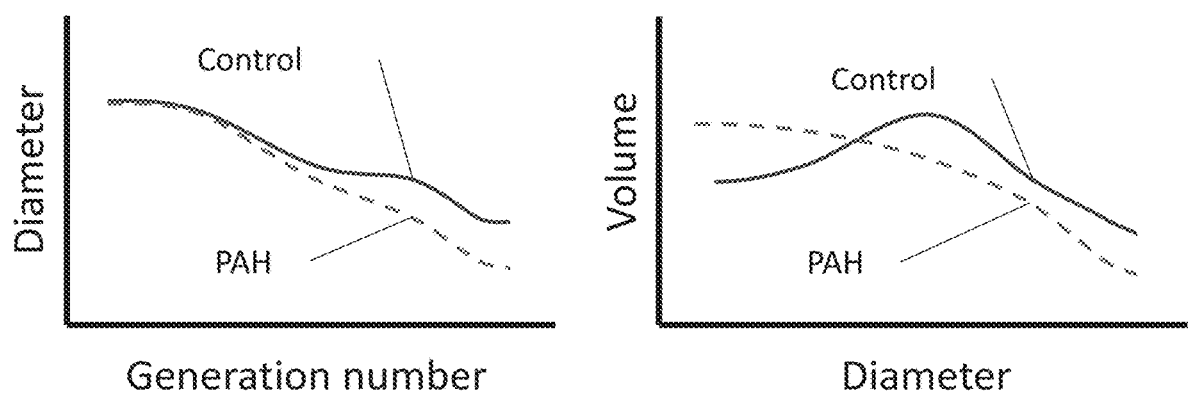
Figure 8A
Figure 8B

METHOD OF SCANNING AND ASSESSING LUNG AND VASCULAR HEALTH

INTRODUCTION

This invention was made with government support under Grant No. HL125806 awarded by National Institutes of Health. The government has certain rights in the invention.

FIELD OF INVENTION

The present invention relates to the field of medical imaging in the absence of contrast agents.

In one form, the invention relates to the field of imaging vessels, particularly blood vessels such as the pulmonary vasculature.

In one particular aspect the present invention is suitable for use as a technique for assessing lung and vascular health.

It will be convenient to hereinafter describe the invention in relation to detecting abnormalities in the pulmonary vasculature that correlate with pulmonary arterial hypertension (PAH) or pulmonary embolism (PE). However it should be appreciated that the present invention is not so limited and can be applied to detection of other irregularities of vasculature in other parts of the body, such as the brain, heart, liver and kidneys provided there is sufficient contrast between the organ tissue and fluid therein. Furthermore the invention is limited to human application and is suitable for a wide range of veterinary applications.

Furthermore, it will be also convenient to hereinafter describe the invention in relation to scanning using X-ray CT, it should be appreciated that the present invention is not limited to that scanning technique and could, for example be used with other forms of scanning including X-ray computer tomography (CT), particularly 4D-CT, MRI, ultrasound or any other scanning method.

BACKGROUND ART

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

Pulmonary arterial hypertension (PAH) is a devastating disease in which the pulmonary vasculature develops progressive resistance to blood flow. This places strain on the right ventricle that must generate higher and higher pressures to maintain cardiac output. The consequences of PAH are progressive and severe hypoxia, right heart failure, and eventual death. Current screening and diagnostic modalities for PAH are not ideal because, among other limitations, non-invasive screening methods, such as echocardiograms, are insensitive to early disease. Furthermore, echocardiographic estimates of pulmonary artery (PA) pressures can both under- and over-estimate actual pressures.

Accurate measurement of pulmonary artery pressure requires invasive right heart catheterization, the gold standard for the evaluation of pulmonary hypertension. For this procedure, a large catheter with pressure transducers is inserted via the jugular vein through the right side of the heart and into the pulmonary artery. Due to its invasive nature, need for specialized technical staff and facilities, and expense, right heart catheterization is not used to assess individual patients' responses to medications or for routine monitoring. Hence, there is a strong need to develop additional non-invasive protocols for diagnosing PAH, and in particular for accurately assessing pulmonary artery pressures.

Over the past 20 years, many drugs have been developed that target discrete and separate pathways involved in PAH, resulting in higher survival and fewer patients requiring lung transplantation. Because the causative molecular pathways involved in the pathogenesis of PAH likely differ among the associated conditions—such as collagen vascular disease, HIV infection, etc.—efficacy to a given therapeutic agent is not at all predictable for a given patient.

Unfortunately, assessment of clinical responses to the wide range of PAH therapeutic agents are critically limited due to the lack of sensitive, accurate clinical endpoints. Mortality, time to clinical worsening (TTCW) and 6-minute walk test distances are the main outcome measures used in studies of new PAH medications, but none are ideal: mortality endpoints require large and extended trials, TTCW is a composite endpoint that varies among studies, and changes in 6-minute walk tests after the onset of therapy do not appear to predict outcomes in pulmonary hypertension.

Thus, clinical improvements that occur in response to PAH drug therapies are not accurately detected by 6-minute walk tests, a mainstay of PAH studies, suggesting that this endpoint is therefore insensitive and may prevent beneficial drugs from coming to market. In other words, the ability to directly assess the effects of novel and promising PAH medications is severely curtailed by the limited read-outs of efficacy available for clinical trials.

Although there have been advances in non-invasive methods such as X-ray computed tomography (CT) in the fields of neurology, cardiology and oncology pulmonary medicine has been held back by the difficulty of obtaining images in which vasculature is clearly visible. While medical contrast agents may improve visibility, they cannot be used when scanning some patients. Furthermore, irrespective of the presence of contrast agents, changes in vasculature caused by disease states or other disorders are still difficult to detect. For example, no method currently exists that allows visualisation of the vasculature affected by PAH.

It is in light of these problems that the current invention has been conceived.

SUMMARY OF INVENTION

An object of the present invention is to provide a non-invasive method of analysing blood vessels in the assessment of disease states and other disorders.

Another object of the present invention is to advance effective functional imaging of vasculature.

A further object of the present invention is to alleviate at least one disadvantage associated with the related art.

It is an object of the embodiments described herein to overcome or alleviate at least one of the above noted drawbacks of related art systems or to at least provide a useful alternative to related art systems.

In a first aspect of embodiments described herein there is provided a method of scanning for vascular ill health using a data set from an in vivo scan, the method including the steps of:

extracting blood vessel location data and blood vessel size data from the scan data set;

selecting a region in the extracted vessel location data; and comparing the size data in the selected region to size data in a corresponding region of a normative data set to determine vascular health.

The data set may be from two-dimensional (2D) or three dimensional (3D) scanning. Preferably the data set is from a 3D scan, but a 2D scan such as a fluoroscopy image may be suitable. Preferably the data set is acquired using X-radiation, such as in X-ray computer tomography (CT) scanning. CT takes a series of 2D radiographic data sets created by X-ray scanning around a single axis of rotation and subjects the data sets to computerised digital geometry processing to generate the 3D scans. It will be understood that use of the term "in vivo" herein, with regard to in vivo images and in vivo scans, refers to the situation where the subject is living. For example, an in vivo lung image would be an image of the lungs, wherein the lungs are located in the living subject (for example by x-ray imaging), rather than an image of lungs that have been excised from the subject.

Typically, the method of the present invention is fully automated. The data sets may optionally be converted to one or more visual images. This may be of assistance for example, if a relevant vessel or relevant region is visually selected. Users of the method may also find the generation of images helpful for their own understanding of which vessels or vessel locations are being examined. However, the use of a computer to perform steps of the method of the present invention is generally preferable because it uses data sets objectively and efficiently.

Preferably, but not essentially, the scan is acquired in the absence of contrast agent. Contrast agents such as iodine are used to assist clear visualisation of an image derived from a scan and are particularly desirable for 2D scans. However, although contrast agents enhance the contrast of structure or fluids within the body in medical imaging, and thus enhance their visibility, adverse medical conditions can be caused by administration of contrast agents. Reactions can range from minor to severe. Risk factors for developing severe reactions include strong allergies, bronchial asthma, cardiac disease and use of certain drugs. Contrast medium induced nephropathy (CIN) is the third most common cause of in-hospital acute renal failure. Accordingly, in some applications it is preferable to use the method of the present invention in relation to in vivo scans carried out in the absence of a contrast agent.

Preferably the normative data set comprises an average of multiple healthy scans. The healthy scans that form the normative dataset may include, or may consist solely of, existing (or historical) scans (e.g. retrospective datasets).

In a second aspect of embodiments described herein there is provided a method of scanning for lung ill health using a data set from an in vivo scan, the method including the steps of:

extracting blood vessel location data and blood vessel size data from the scan data set;

selecting a first region and a second region in the extracted vessel location data; and comparing the size data in the first region to the size data in the second region to determine vascular health.

In a third aspect of embodiments described herein there is provided method of assessing lung disease treatment efficacy using a pre-treatment data set from an in vivo scan and a post-treatment data set from an in vivo scan, the method including the steps of:

extracting blood vessel location data and blood vessel size data from the scan data sets;

selecting a region in the extracted vessel location data from either the pre-treatment scan data set or post-treatment scan data set; and comparing the size data in the selected region to size data of a corresponding region in the other data set to assess the efficacy of the treatment.

The method of the present invention thus provides direct visualisation of the effects of lung disease treatment and a way to measure outcomes in studies on new drugs and treatment regimes. The method is likely to be particularly useful for directly visualising the effects or vasodilator and other therapies for pulmonary hypertension and the efficacy of new drugs for pulmonary hypertension.

Accordingly, in a fourth aspect of embodiments described herein there is provided method of assessing a lung disease treatment using a data set from an in vivo lung scan performed prior to application of the treatment to a patient and a data set from an in vivo lung scan performed after application of the treatment, the method including the steps of:

extracting blood vessel location data and blood vessel size data from the scan data sets;

selecting a region in the extracted vessel location data from either the pre-treatment scan data set or post-treatment scan data set; and comparing the size data in the selected region to size data of a corresponding region in the other data set to assess the efficacy of the treatment.

In a preferred embodiment the treatment comprises application to the patient of a drug such as a pharmaceutical active or an immuno-therapeutic agent.

The data set may be from a 2D or 3D scan. Preferably the data set is from a 3D scan (such as a 3D image), but a 2D scan such as a fluoroscopy image may be suitable.

It will also be appreciated that the scan may be converted to a visual image. This may be of assistance in selecting a relevant vessel or relevant region.

The step of extracting blood vessel location and size data preferably includes applying a filter to the scan data set (such as, to a three-dimensional in vivo image) to provide a probability field and a scale field. Vessel segmentation may be performed on the probability field to extract a vasculature tree from the probability field. One suitable vessel segmentation method is described for example in co-pending Australian Application No. 2016900817 titled "Method and System for Pulmonary Imaging", and corresponding to International Application No. PCT/AU2013/000390.

It may additionally be advantageous to map the scale field to the segmented vasculature tree to quantify the geometry of the vasculature tree.

Analysis of the size data may include for example, comparing parameters such as average vessel size in the region distribution of vessel size/diameter in the region, e.g.:

height of the major peak height of the major and minor peaks height difference between/ratio of the major and minor peaks median value for all vessels (i.e. at what vessel size are you at 50% of all vessels)

histogram/line plot of vessel size (e.g. diameter, cross sectional area, etc.) against generation number histogram/line plot of vessel size (e.g. diameter, cross sectional area, etc.) against path length vessel length against vessel size (e.g. diameter, cross sectional area, etc.)

The present invention can be utilised with other types of size/measurement such as vessel generation—vascular diameter for a given generation of vessels and differences between healthy and diseased lungs, changes in vascular diameter from one generation to the next, and the degree of tapering in a particular vessel segment (so the ratio of proximal to distal vascular diameter for that segment). Furthermore, parameters such as the number of vessels per lung volume may be indicative of certain diseases and recruitment or de-recruitment of collapsed or "dormant" vessels.

From this it will be also apparent to the person skilled in the art that the method of the present invention can be applied to a wide variety of disorders and disease states. In addition to diagnosis of PAH and PE, the person skilled in the art will realise that the method of the present invention may be suitable to detect disease states such as congestive heart failure, acute lung injury, and lung cancer.

For example, when a patient is in heart failure the pressures in their pulmonary veins increases (as reflected by an increase in left atrial pressure measured by right heart catheter, also known at the pulmonary capillary wedge pressure). Often when a patient presents with shortness of breath medical practitioners have to decide whether they have a cardiac disease (heart failure) or a pulmonary disease (pulmonary embolism, other disease like asthma or COPD). Being able to compare the size of pulmonary veins (which, going to the left side of the heart from the lungs, might be engorged in heart failure) to the size of the pulmonary arteries (which leave the right side of the heart) might generate patterns that are specific for congestive heart failure as compared with other causes for shortness of breath.

The method of the present invention may also be useful for characterising the vascular changes that develop over time in patients, particularly children, with congenital heart disease who develop pulmonary hypertension. Following vascular morphology over time in children with heart defects might be used down the road to determine when therapy or surgery for heart defects needs to be initiated.

The method of the present invention may also be useful to determine if the responses of the pulmonary vessels during acute lung injury are pathological (dilating in areas of injury instead of constricting) which may lead to development of therapies designed to address this pathology.

The method of the present invention may also be useful in disease states such as emphysema as a means of determining the severity of the condition, possibly in combination with existing methods of monitoring such as blood oxygen saturation and blood gas analysis.

The method of the present invention may be useful for the detection of lung cancer or responses to chemotherapy based on the patterns of blood vessels in an area of the lung, given that lung cancers are by nature highly vascular. For example, a patient with lung cancer may have a CT scan which shows lots of abnormal blood vessels supplying an area of the lung where cancer is located. Following chemotherapy the patient's repeat CT scan may show that all the abnormal vessels have shrunk down/clotted off and this is a more accurate/sensitive marker of response to chemotherapy than the current "tumour size shrinks" readout of the prior art.

Alternatively, if the patient has the lung cancer resected, this would be followed immediately by a CT scan to establish a baseline vascular pattern after the cancer has been cut out. Hypothetically, the patient would undergo repeat scans every 4 to 6 months because increased vascular density in the region adjacent the prior location of the cancer precedes any visible mass (if the signal from tumour for vessel growth happens before mass is visible). Use of the method of the present invention may facilitate earlier detection of recurrent cancer and allows earlier initiation of further chemotherapy, surgery or other appropriate treatments.

The method of the present invention can thus not only be used as a diagnostic in respect of lung health, but also as part of individual patient therapy.

In a fifth aspect of embodiments described herein there is provided a method of treating a patient suffering a lung disease using a first data set from a first in vivo lung scan and a second data set from a second in vivo lung scan performed after application of a treatment regime, the method including the steps of:

extracting blood vessel location data and blood vessel size data from the scan data sets;

selecting a region in the extracted vessel location data from either the first scan data set or the second scan data set; and comparing the size data in the selected region to size data of a corresponding region in the other data set, assessing the efficacy of the treatment, and determining a further treatment regime for the patient.

In this manner the patient can be monitored using the method of the present invention and their treatment regime adjusted appropriately based on the lung response. Each round of treatment in the regime can be tailored to the response.

Other aspects and preferred forms are disclosed in the specification and/or defined in the appended claims, forming a part of the description of the invention.

In essence, embodiments of the present invention stem from the realization that scans, preferably contrast-free CT scans, can be used to directly visualise pulmonary vasculature, preferably in three dimensions, and accurately measure the diameters of the pulmonary arteries and then, on further analysis, be used to accurately diagnose disease states such as PAH and grade its severity. While specific methods of processing data from images are disclosed in the prior art, the specific combination of methods and method steps have not hitherto been used.

Advantages provided by the present invention comprise the following:

a non-invasive diagnostic for assessing lung and vascular health;

a test to visualise the response of the pulmonary vascular bed to therapies such as pulmonary arterial hypertension therapies;

ability to measure outcomes in studies on new drugs and treatment regimes;

ability to accurately diagnose disorders such as pulmonary arterial hypertension and grade its severity without the need for invasive procedures;

ability to expedite and maximise treatment of vascular disorders;

ability to monitor and appropriately adjust treatment regimes based on the lung response;

replacement of invasive measures such as right heart catheterization, with non-invasive measures in the management of disorders such as pulmonary arterial hypertension.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiments taken in conjunction with the accompanying drawings, which are given by way of illustration only, and thus are not limitative of the disclosure herein, and in which:

FIG. 7A is an example of the comparison step, in particular a line plot of the vasculature distribution in 4 patients (n=2 controls and n=2 PAH);

FIG. 7B is another example of the comparison step, in particular a histogram plot of vasculature density change index from the data in FIG. 7A;

FIG. 8A is a line plot of vessel diameter against generation number;

FIG. 8B is a line plot of volume (total vessel volume) against vessel diameter;

DETAILED DESCRIPTION

Figure 1:
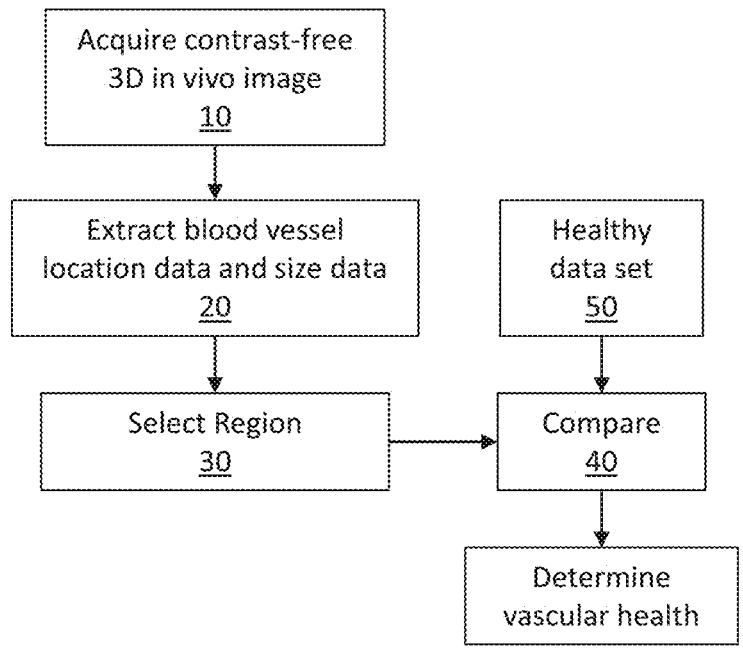
FIG. 1 is a flow chart of a first embodiment of the invention for determining vascular health.
Figure 2:
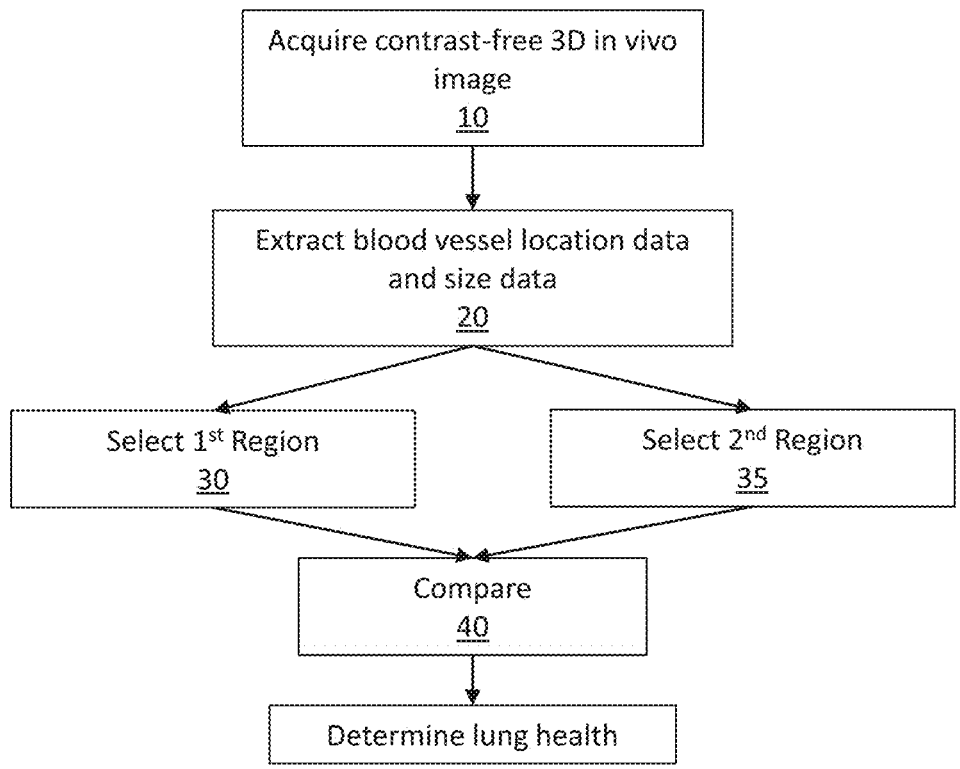
FIG. 2 is a flow chart of an alternative embodiment of the invention for determining vascular health.
Figure 3:
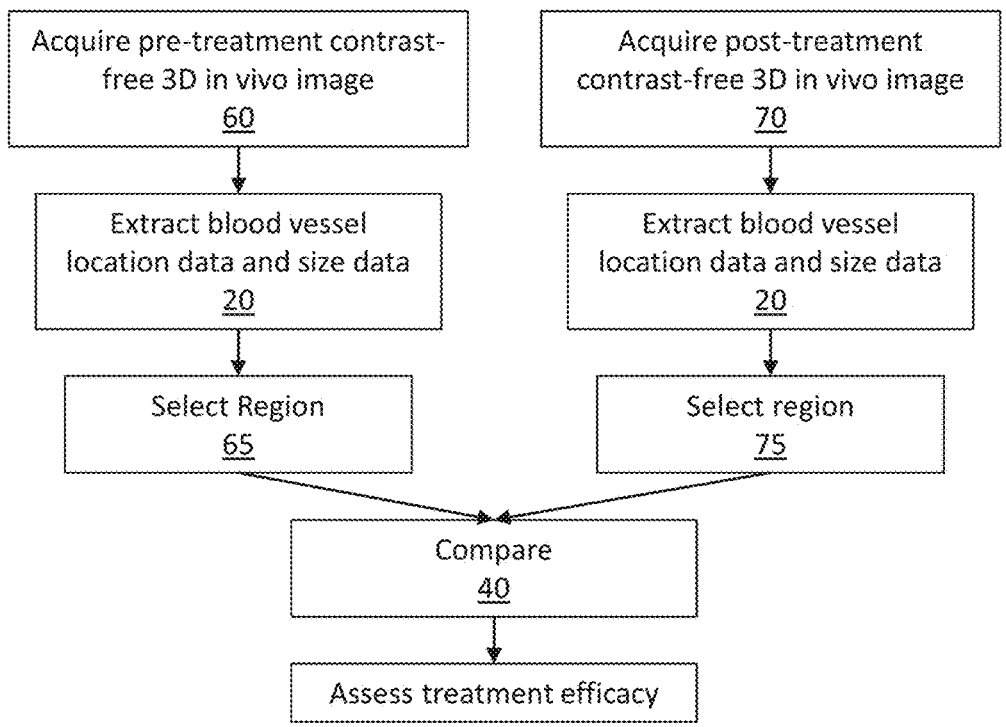
FIG. 3 is a flow chart of an alternative embodiment of the invention for assessing treatment efficacy.

FIGS. 1 to 3 show three different aspects of implementation of the present invention. Referring first to FIG. 1, there is a method of scanning for vascular ill health, such as pulmonary hypertension or increased pulmonary artery pressure, from a three-dimensional in vivo image 110 acquired 10 in the absence of contrast agent. Blood vessel location data 120 and blood vessel size data 121 is extracted 20 from the three-dimensional image 110. Once the vessel location 120 and size 121 data has been extracted 20 a region 130 is selected 30 in the extracted vessel location data 120 for analysis. The size data 121 in the selected region 130 is then compared 40 to size data in a corresponding region of normative data 50. By performing this comparison 40 it is possible to determine whether the blood vessels, such as the pulmonary arteries, are in a healthy range (i.e. closely match the normative data set), or are in an unhealthy range (i.e. significantly deviate from the normative data set), thereby allowing a determination of vascular health. In particular, regarding PAH, the blood vessel diameter decreases, or shrinks, so that the vessels are narrower.

The step of acquiring 10 a contrast-free 3D in vivo image 110 can be performed using any suitable medical imaging method. For example, an X-ray computed tomography (CT) scan may be performed as a "breath hold", in which the patient holds their breath during the scan. In order to remove the movement of the heart, which results in blurring and has a physical impact on the position of the lungs and the blood vessel size, the breath hold CT scan may be "gated" to the cardiac cycle, providing greater CT resolution. Alternatively, the method can be applied to existing (or historical) contrast-free imaging data (e.g. data from a former patient's previous scan).

4D imaging techniques, such as 4DCT, which image moving organs (such as a breathing lung) can also be used to acquire the contrast-free 3D in vivo image 110. 4DCT essentially acquires a time series of 3D images, allowing a single 3D image to be extracted from the full 4D data set (with the preferred 3D image being at peak inspiration, when the signal to noise ratio between the lung vasculature and the lungs themselves is the greatest).

Alternatively, a series of 2D images can be acquired from multiple viewing angles and reconstructed to form a 3D image (e.g. a series of 2D X-ray images using a cone beam computed tomography reconstruction (CBCT)). It is envisaged that any of CT, 4DCT, CBCT, MRI or any other medical imaging method could be used to acquire 10 the contrast-free 3D in vivo image 110. When referring to scans of the lungs (e.g. chest X-rays), for the purpose of investigating lung vasculature, these techniques may be referred to as contrast free pulmonary angiography (CFPA) techniques. A benefit of acquiring images without contrast agent is that it avoids known adverse side effects from the administration of contrast agent, such as skin lesions, dizziness, vomiting, life-threatening arrhythmia, seizures and contrast medium induced nephropathy (CIN).

Figure 4:
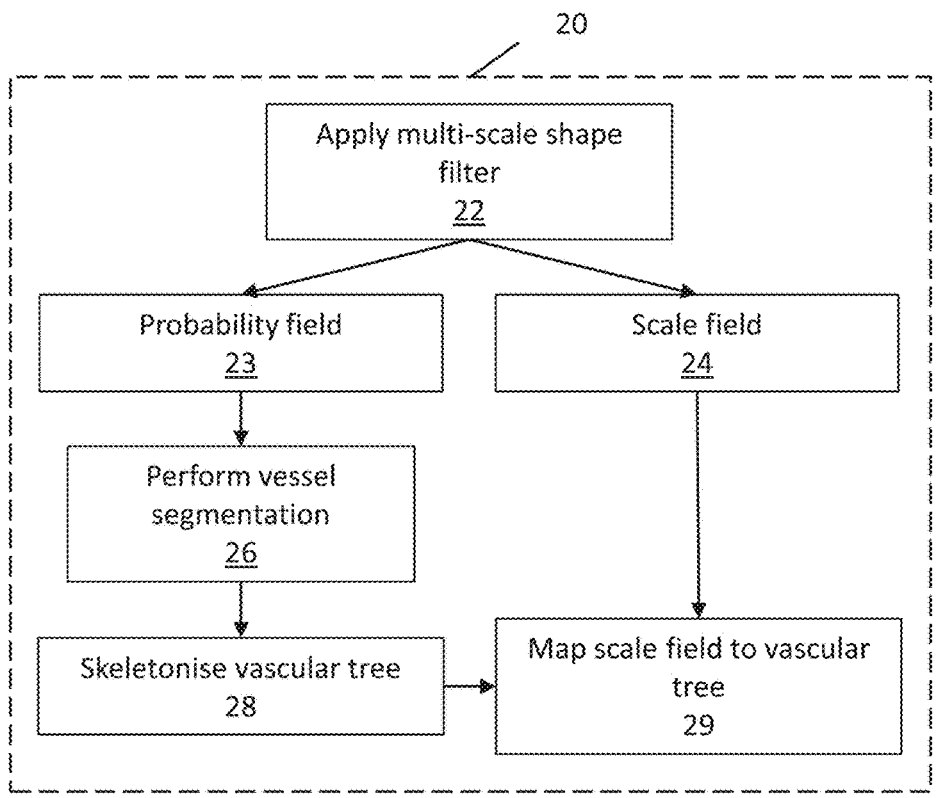
FIG. 4 is a flow chart of the extract blood vessel location data and size data step shown in FIGS. 1 to 3.
Figure 5:
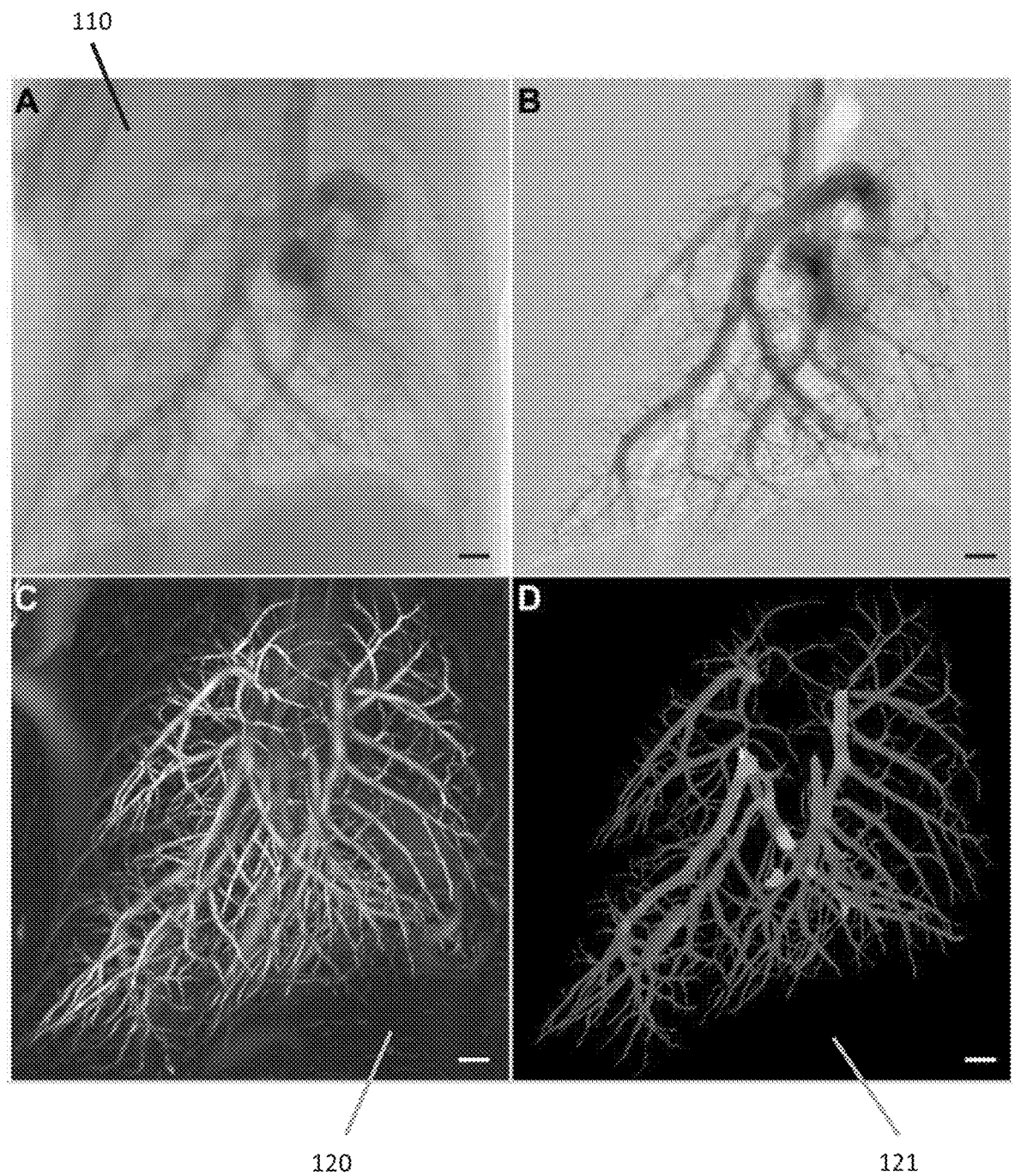
FIG. 5A is a typical 2D projection image of the lungs generated using laboratory X-ray source.
FIG. 5B is a typical 2D projection image of the lungs generated using laboratory X-ray source with iodinated contrast agent in the lung vasculature.
FIG. 5C is an isometric view of the probability field extracted by using the multi-scale shape filter.
FIG. 5D is an isometric view of the segmented vasculature (from the probability field in FIG. 5C) coloured by the scale value at the centreline of each point in each branch.

Referring now to FIGS. 4 and 5, the step of extracting 20 blood vessel location data 120 and blood vessel size data 121 will now be discussed. While there are multiple methods for extracting such location and size data a preferred method is discussed hereafter. First, a shape-based filter, shown as multi-scale shape filter 22, is performed on the 3D in vivo image 10. The shape-based filter is applied to every voxel in the 3D image 10 in order to determine the probability that the voxel in the image 10, at a given scale, is part of the specified shape. This produces a probability field (also known as a probability image) of the scale. The shape-based filter can be applied at multiple scales (i.e. a multi-scale shape filter 22), thereby creating multiple probability fields, one for each scale. This creates probability data and scale data that can be interrogated. It will be understood that the 3D in vivo image may be binned (e.g. 2×2×2 image binning could be used to reduce the 3D image to ⅛ of its original size). Binning can assist in removing artefacts from the image and/or avoiding artefacts being introduced during the shape-based filtering.

An overall probability field 23 (or image) can be formed by combining the multiple single scale probability fields (see FIG. 5C). This is conducted by comparing the probability of the first voxel in each of the probability fields and selecting the highest probability, comparing the probability of the second voxel in each of the probability fields and selecting the highest probability, and so on for all voxels. The scale at which the highest probability occurs is also recorded for each voxel, thereby creating a corresponding scale field 24 (or image). The terms field and image are used here somewhat interchangeably when referring to the probability and scale fields, as the data in the probability and scale fields can be displayed visually, if desired, as an image. Essentially the probability field represents the probability that a voxel in the three-dimensional in vivo image is a part of the shape of interest, and the scale field represents the filter size that yields the greatest probability that the voxel belongs to the shape of interest.

The multi-scale shape filter 22, preferably Hessian based multi-scale shape filter based on Frangi et al. (Frangi et al, Medical Image Computing and Computer-Assisted Interventation—MICCAI '98 (eds. Wells, W. M., Colchester, A. & Delp, S.) 130-137 (Springer, 1998), can be used to detect shapes such as plate-like structures, tubular structures, blob structures, etc. For example, when investigating the vasculature of the lungs the shape based filter 22 will interrogate the 3D image 10 for tubular shapes or structures. In addition, because the vessels in the lung are not of a single diameter, the shape-based filter is run at multiple scales, in order to capture tubular structures at multiple diameters. When searching for tubular shapes the filter is sometimes referred to as a "vesselness" filter, with the probability field representing the vesselness. In order to simplify implementation of the multi-scale shape filter 22 the image may be inverted before the filter is applied to the 3D image. Alternatively, the filter may be designed to effectively invert the image in the application of the filter (i.e. the inversion may be carried out as part of the filtering process).

Once the overall probability field 23 has been constructed the vasculature tree can be segmented 26 from the 3D image 10. This is achieved by performing a region growing operation on the probability field 23 to provide a binary image (or data field) of the lung vasculature. Both the arteries and the veins can be extracted by using this technique, and depending on the vasculature of interest a user may choose to only extract either the arteries or the veins. For example, emboli generally become stuck in veins, except for in the lungs, where they only become stuck in the arteries. The rest of the specification will consider only the pulmonary arteries.

The region growing operation may be any suitable region growing operation, such as a flood fill or form filling operation. This step is performed by choosing a recognisable portion of the lung vasculature in the probability field 23, with the region growing operation connecting the branches in the vasculature tree. As an example, the region growing operation can be a flood-fill segmentation using Avizo (FEI VSG, France). This process results in a binary image that has a single flood-filled section, thereby segmenting the vasculature from the original 3D CT reconstruction (see, FIG. 5D, which has had the surface of the segmented vasculature coloured by the diameter). In this way the probability field is both binarised and segmented in a single step. It will be understood that this could be carried out in two separate steps, if desired.

Once the vasculature has been segmented a skeletonisation procedure 28 is used to determine the centreline in each branch of the segmented vasculature. For example, the skeletonisation procedure may be the same technique used in Sato, M. et al. (Sato, M. et al, TEASAR: tree-structure extraction algorithm for accurate and robust skeletons, 8th Pacific Conference on Computer Graphics and Applications, 2000. Proceedings 281-449 (2000). doi:10.1109/PCCGA.2000.883951). This provides a skeletonised vascular tree (also referred to as a centreline tree).

The scale value at the centre of the vessel provides a measure of the vessel diameter. Therefore, once the skeletonised vasculature tree has been extracted 28 from the probability field 23, the scale field 24 is mapped 29 onto the skeletonised vasculature tree 28, thereby quantifying the geometry of the vascular tree. In other words, for each location in the skeletonised vasculature tree the corresponding scale value is extracted from the scale field 24, thereby providing a single combined 3D data set 29 (or image) with geometrical information, including positional information (from the skeletonised vasculature tree 28 which was extracted from the probability field 23) and relative size information (from the scale field 24). The scale relates to a measure of the diameter, or calibre, of the vessel, in voxels. If the voxel size is known then the scale can be converted into a measurement in millimetres (or any other desired length unit). Calibration of the system can be performed by scanning tubes of known diameters in order to determine the voxel size. Before the skeletonised vasculature tree 28 is mapped 29 to the scale field 24, either the skeletonised vasculature tree 28, the scale field 24, or both, can be smoothed, in an attempt to improve the accuracy of the geometric wuantification of the vascular tree.

Further information of the method for extracting blood vessel location data and blood vessel size data, particularly segmentation, can be found in co-pending Australian Application No. 2016900817 titled "Method and System for Pulmonary Imaging", and corresponding to International Application No. PCT/AU2013/000390.

The vessels are preferably identified, beginning with the left and right pulmonary arteries, to the 6th generation according to Boyden nomenclature (although other nomenclatures, or even a simple generation numbering is also possible). Beyond this, vessels are identified by generation. Characterising the vascular tree in this way allows extraction of a range of different measurements from the segmented vasculature. By identifying vessels according to Boyden nomenclature and generation it is possible to compare size data of equivalent vessels between lungs.

Figure 6A:
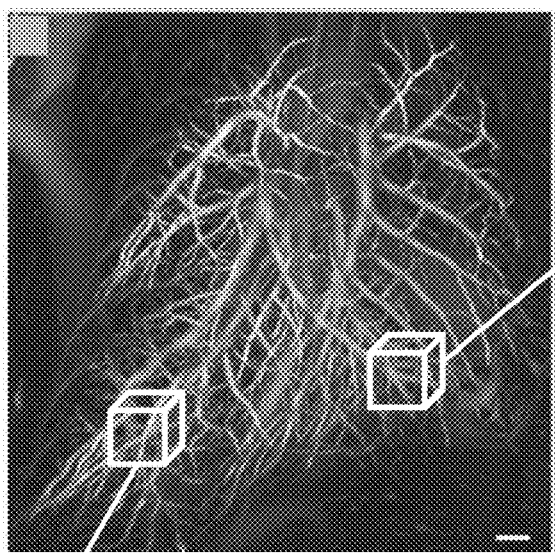
FIG. 6A is an isometric view of the probability field shown in FIG. 5C with two regions of interest shown.
Figure 6B:
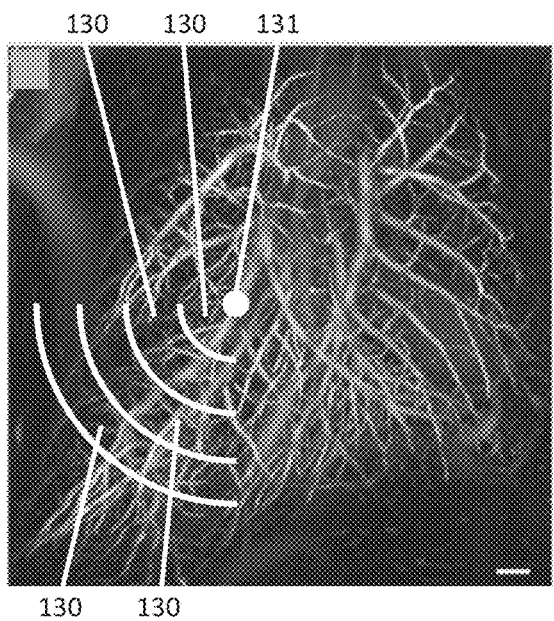
FIG. 6B is an isometric view of the probability field shown in FIG. 5C with an alternative method of defining the region.
Figure 6C:
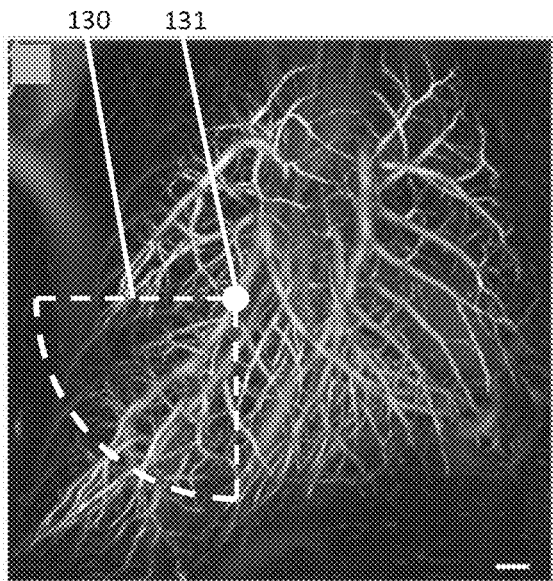
FIG. 6C is an isometric view of the probability field shown in FIG. 5C with another alternative method of defining the region.

Referring now to FIGS. 6A to 6C, the step of selecting a region will be discussed. For visual clarity FIGS. 6A to 6C use the probability field 120 as the background image rather than the segmented vasculature. It will be appreciated that the probability field 120 and the segmented vascular in fact look similar in their representation of the pulmonary vasculature. Referring first to FIG. 6A, a region 130 is highlighted in the segmented vasculature. The region 130 is shown as a three-dimensional volume, and can be located in any desired area of the lung vasculature. The region 130 is shown as a cube, however it could be cuboid volume, or any other volume of interest (e.g. a pyramid or cone volume). The region could also be defined as an anatomical region, such as a sub-lobe, an entire lobe in the lung, an entire lung (i.e. one of the pair of the lungs), or the entire lungs (i.e. both lungs). Alternatively, referring to FIG. 6B, the region 130 may be defined by a specific generation of blood vessel (e.g. the $1^{st}$, $2^{nd}$, $3^{rd}$ etc. generation), or by defined by the distance (or range) of the vascular path (i.e. the path length) from a starting point 131 in the vasculature (as a surrogate for selection by specific generation). Alternatively, referring to FIG. 6C, the region 130 may be defined as the entire vasculature distal to a point 131 in an artery.

Once the region 130 has been selected 30 the size data 121 in the selected region 130 is compared 40 to size data 121 in the normative data set, in order to determine vascular health. It is envisaged that the normative data set will be formed from a combination of known healthy data sets (e.g. from CT scans of people with lungs that are free from lung disease of pulmonary vascular problems) in order to produce a generic normative data set. In other words, the normative data set is an average of multiple healthy scans. It is also envisaged that the normative data set may instead have a data range, rather than a discrete value, for each point (e.g. location) in the data set. The comparison can then determine if a patient is outside of the normative range.

It will be understood that the normative data set does not need to be a three-dimensional image in which a region is selected and analysed, and could instead be a data table from which the size data from the corresponding region is extracted. For example, because the vasculature is identified by Boyden nomenclature and vessel generation it is possible to have the size data for each generation of the normative data set already generated, so that when a specific generation in the segmented vasculature is chosen a direct comparison can be made without interrogation of the normative data set.

The comparison 40 involves comparing the size data 121 extracted from region 130 in the segmented vasculature to the size data 121 from the normative data set. For example, the comparison may involve a statistical analysis of the size data. For example, the data in the selected region 130 could be analysed to determine the average scale (or diameter) of the blood vessels within the region 130, which would then be compared to the average scale (or diameter) of the blood vessels in the corresponding region in the normative data set. Pulmonary arterial hypertension (PAH) patients experience narrowing of the pulmonary artery vessels and, as a result, detecting a change (e.g. a lowering) of average vessel scale (or diameter) is indicative of PAH. In other words, by comparing the size data in the selected region 130 to size data in a corresponding region of a normative data set, vascular health can be determined. This data could be used to not only detect the presence of PAH, but also the degree of PAH. Alternatively, two of the same vessels can be directly compared between a PAH scan and a normative data set, if the same vessel can be identified (e.g. using the Boyden nomenclature). The comparison 40 may be performed automatically, for example by a computer.

Referring now to FIG. 7A, another example of a statistical comparison 40 is shown. In particular, FIG. 7A shows vascular diameter distributions in 4 patients (n=2 controls or normative data sets, and n=2 PAH), with vascular diameter shown on the x-axis and probability (surrogate for number amount) shown on the y-axis. The region used in FIG. 7 is the entire lungs. The two control patients have distributions with two distinct peaks, a primary peak at approximately 7 mm diameter and a secondary peak at approximately 10 mm diameter (i.e. the healthy patients exhibit a bimodal distribution for vascular diameter). In contrast, each of the two PAH patients have a much stronger primary peak at approximately 8 mm diameter, and a much smaller secondary peak at approximately 10 mm. This demonstrates that PAH alters the vascular diameter distributions, and can therefore be used to determine vascular health. In other words, by comparing the vessel distribution in the selected region 130 to the vessel distribution in a corresponding region of a normative data set, vascular health can be determined.

Referring now to FIG. 7B, the vascular density change index (ratio of primary peak to the secondary peak) is plotted for each patient. As can be seen, the vascular density change index for the control patients is between 1 to 1.5, and the vascular density change index for the PAH patients is between 2 to 3.5. This demonstrates that a ratio from data in the vessel distribution can therefore be used to determine vascular health. Alternatively, the vasculature diameter of the peaks may be set by the normative data set, and then the probability of the PAH data set read off for comparison. This method is beneficial if the PAH set has, for example, only a single peak. In addition, instead of searching for a peak it may be easier to find the vessel diameter under which 50% of the vessels are smaller in each of the PAH and normative data sets. Alternatively, the 50% diameter could be determined in the normative data set and then be used to determine what percentage of vessels are below the 50% normative diameter (i.e. is envisaged that the percentage will increase in PAH patients).

Referring now to FIG. 8A, an alternative form of size data is shown for comparison. In particular, FIG. 8A is a line plot of diameter (y-axis) against vessel generation number (x-axis) for the entire lungs of both a normative and a PAH scan. The diameter shown could be the modal diameter, the average diameter, or any other suitable measurement (FIG. 8A shows the modal diameter). As can be seen, the lower generations of the control and PAH scans have very similar modal diameters, but as the generation number increases the difference between the modal diameter for the PAH scan and the modal diameter for the control scan becomes more apparent (i.e. the PAH scan has lower modal diameters in the higher generation numbers), and can therefore be used to detect PAH. This demonstrates that a comparison of a statistic of the size data at one or more specific vessel generations can be used to determine vascular health. Alternatively, instead of using the vessel generation to divide up the pulmonary vasculature (which can be difficult) the path length (i.e. distance) from a chosen point in the vasculature can be used (as the vessel centreline data has already been extracted from the segmented vasculature).

Figure 8C:
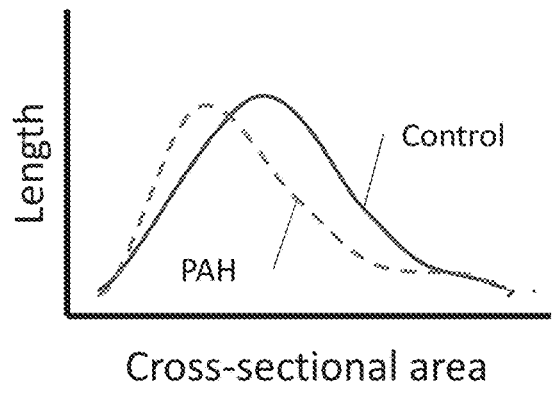
FIG. 8C is a schematic line plot of length (total vessel length) against vessel cross-sectional area.
Figure 8D:
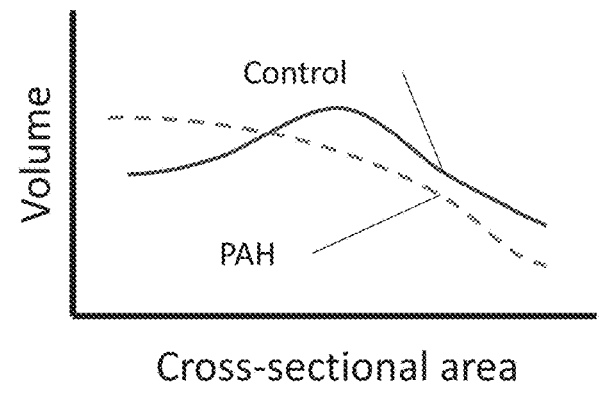
FIG. 8D is a schematic line plot of volume (total vessel volume) against cross-sectional area.

Referring now to FIGS. 8B to 8D, alternative forms of size data is shown for comparison. FIG. 8B plots the volume against the diameter for a region of the lung. In other words, FIG. 8B shows the total volume of vessels for a given diameter. While only a schematic, it is predicted that such a plot (or probability density function—PDF) will show differences between PAH patients and a normative data set. Alternatively, the length (i.e. total length) could be plotted against vessel diameter, or the number (i.e. number of vessels) could be plotted against vessel diameter. FIG. 8C plots the length (i.e. total vessel length) against the cross-sectional area for a region of the lung. The area under the curve in this graph corresponds to the volume. FIG. 8D plots the volume against the cross-sectional area for a region of the lung. It will be understood that other forms of size data could be plotted for comparison. In addition, it will be understood that the size data could be normalised, if desired.

Figure 8E:
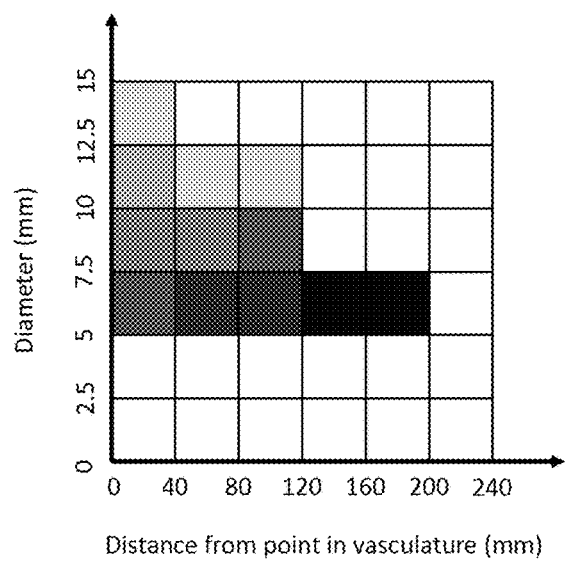
FIG. 8E is a heat map of diameter against path length from a point in the vasculature for a healthy patient.
Figure 8F:
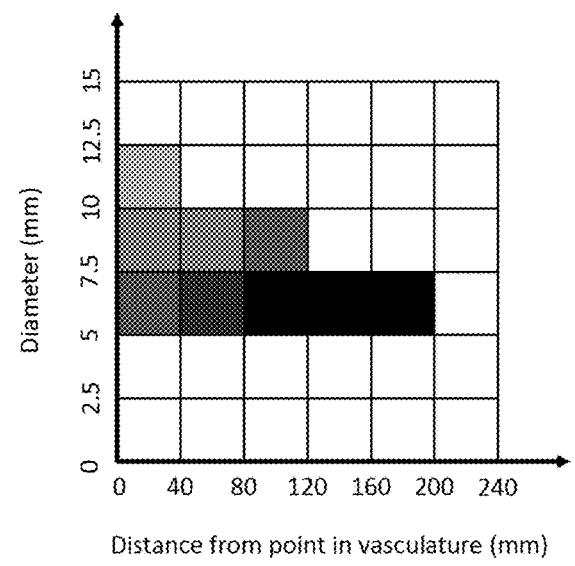
FIG. 8F is a heat map of diameter against path length from a point in the vasculature for a patient with PAH.

Referring now to FIGS. 8E and 8F, an alternative form of size data is shown for comparison. FIG. 8E is a theorised heat map of diameter against path length for a healthy patient. Each column in the heat map shows the distribution of diameter sizes at a given path length from a point 131 in the vasculature. FIG. 8F is the corresponding theorised size data for a patient with PAH. It is believed that size of the vessels will reduce, thereby compacting the heat map in the vertical direction. The diameter is shown as not going below 5 mm, which is provided in the theorised plots as an example of the minimum measurement of the system.

Referring now to FIG. 2, another implementation of the invention is shown, in which the method involves scanning for lung ill health from a three-dimensional in vivo image 110 acquired 10 in the absence of contrast agent, however, without the need for comparison to a normative data set. Blood vessel location data 120 and blood vessel size data 121 is extracted 20 from the three-dimensional image 110. Once the vessel location 120 and size 121 data has been extracted 20 a first region 130 is selected 30 in the extracted vessel location data 120, and a second region 135 is selected 35 in the extracted vessel location data 120. The size data 121 in the first selected region 130 is then compared to the size data 121 in the second selected region 135. By comparing multiple regions of a single subject's (such as a human patient) scan it is possible to determine whether the compared regions of the lung are homogeneous or heterogeneous. Heterogeneity is a known indicator of ill lung health, and vascular health can be inferred from this information.

It is envisaged that the multiple regions in the single scan may be such that the entire lungs are covered by the regions, and that the comparison therefore compares each region of the lung to all other regions of the lung, providing a map of homogeneous areas (or regions) and heterogeneous areas (or regions). Similar techniques to those described above can be used to compare the two regions 130, 135.

Referring now to FIG. 3, another implementation of the invention is shown, in which the method involves assessing lung disease treatment efficacy from a pre-treatment three-dimensional in vivo image acquired 60 in the absence of contrast agent and a post-treatment three-dimensional in vivo image acquired 70 in the absence of contrast agent. Blood vessel location data 120 and blood vessel size data 121 is extracted 20 from both the pre-treatment 112 or post-treatment 114 images. Once the vessel location 120 and size 121 data has been extracted 20 a region 130 is selected 30 in either the pre-treatment 112 or post-treatment 114 images, for this example the region is selected 65 in the pre-treatment image 112. The size data 121 in the selected region 130 is then compared 40 to size data 121 of a corresponding region in the other image, in this case the region selected 75 in the post-treatment image 114. By performing this comparison 40 it is possible to assess the efficacy of a lung disease treatment. Preferably the regions for comparison are in exactly the same position. Again, similar techniques to those described above can be used to compare the two regions.

A benefit of the method shown in FIG. 3 is that it can provide clinical trials with a non-invasive tool to assess the effects of medications on the pulmonary vasculature, allowing an understanding the mechanisms of disease and the responses of the vasculature to new therapeutics.

It is envisaged that the three methods described above (i.e. relating to FIGS. 1 to 3) could be combined. For example, the third method described (i.e. relating to FIG. 3) could also include either comparing the region to a normative data set (i.e. from FIG. 1), or comparing the region to a second region in the same scan (i.e. from FIG. 2), or it could include both of these steps.

Once the comparison 40 has been completed the results may be displayed to a user (e.g. a doctor). The results can be displayed as a visualisation on a computer screen (e.g. 2D or 3D visualisation), or as a report (e.g. a hard or soft copy report), or any other suitable way. It is envisaged that the results may be displayed as an overlay on the original three-dimensional image 10 of the vasculature. For example, areas in which PAH have been identified may be highlighted to bring these areas to the attention of the doctor. Alternatively, the results may be graphically displayed, for example as shown in FIGS. 7 to 8F.

It is envisaged that the three-dimensional in vivo image may be acquired by one user, such as a hospital technician, and analysed (i.e. the steps of applying the filter and performing the analysis) by another user, such as an analysis company. In other words, the method for the first user is to acquire a three-dimensional in vivo image 10 in the absence of contrast agent (which may be a simple standard CT, such as a helical or spiral CT), and the method for the second user is to extract the vessel location and size data 20 and perform the comparison 40.

Figure 9:
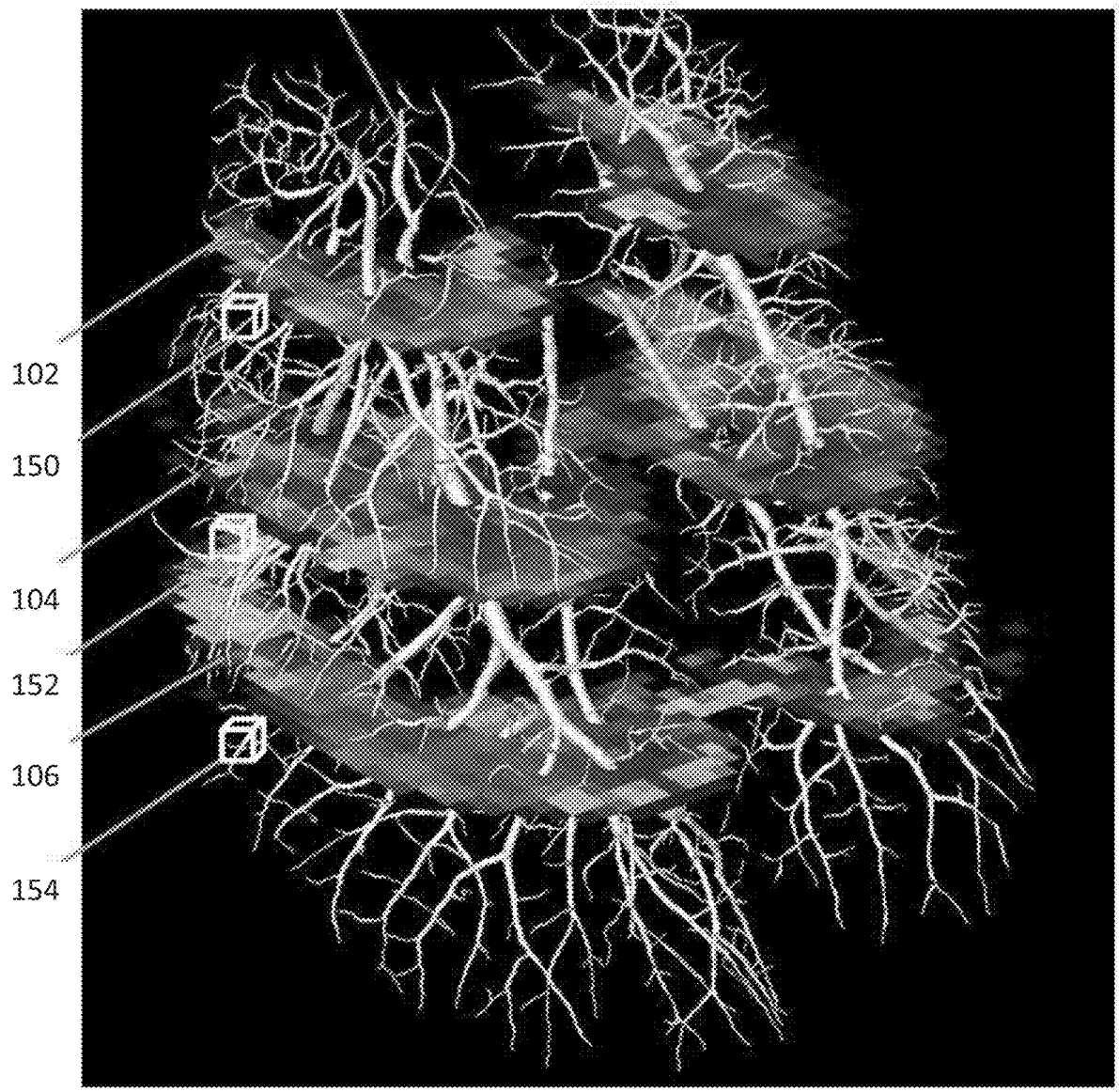
FIG. 9 is a visualisation of the segmented vasculature with regional motion information overlayed at three slice positions.

Referring now to FIG. 9, it is envisaged that the detailed geometric information from the method described herein could be combined with local (or regional) motion measurements in order to calculate a surrogate of the ventilation/perfusion (V/Q) ratio (hereafter simply referred to as V/Q or ventilation perfusion). In particular, the motion of a portion of the lung can be compared to the scale of the vasculature in the region of the portion of the lung to obtain a ventilation/perfusion measure. FIG. 9 shows the segmented vasculature with motion information overlayed at three slice positions 102, 104, 106. The regional scale information can be used as an estimate of the blood flow to a particular region (indicative of perfusion), and can be combined with local motion measurements (indicative of ventilation). Such measurements would require both a three-dimensional in vivo lung image (for vasculature tree information) and a time series of lung images (for motion measurements). The three-dimensional in vivo lung image can be acquired as described above (e.g. a non-contrast CT scan). The series of lung images could be only two images from which lung motion at that point in the respiration cycle can be determined, or the series of lung images could include a complete respiration cycle, thereby allowing the lung motion of the entire respiration cycle to be measured. Again, the imaging, for the vasculature measurements, could be gated to breathing, the cardiac cycle, or both.

The motion of a portion of the lung can be calculated by any suitable technique, however it is preferably measured using Computer Tomographic X-ray Velocimetry (CTXV), as described in U.S. Pat. No. 9,036,887 B2, titled "Particle image velocimetry suitable for X-ray projection imaging", the entirety of which is incorporated herein by reference. CTXV uses X-ray images taken from multiple projection angles in order to measure regional three-dimensional motion of the object, in this case the lungs. The motion tracking in CTXV is based on a well-known technique called particle image velocimetry (PIV), in which the displacement of a region is calculated by selecting a region in the first image of a time series and statistically correlating the selected region to the second image in the time series. The motion measurements can therefore be 2D or 3D measurements of displacement, velocity, expansion (or ventilation), or any other suitable motion measurement. The flow in the airways can also be calculated from the motion measurements.

CTXV is generally performed for multiple regions in the image, thereby providing regional motion measurements throughout the image. Referring specifically to lung imaging, CTXV provides multiple regional motion measurements of portions of the lung, providing local lung movement and expansion measurements. CTXV can be performed at high spatial resolution, meaning that there may be multiple motion measurements in the region 130 of the lung selected for comparison. If this is the case the multiple motion measurements can be averaged. It is also envisaged that the ventilation/perfusion will be assessed at multiple portions of the lung (i.e. there will be multiple lung portions).

Before the ventilation can be compared to the perfusion the data from the two scans are associated with each other (e.g. to compensate for different resolution scans). The two data sets are also rotationally aligned.

By comparing the motion, or a parameter derived from the motion (e.g. the expansion, also sometimes referred to as the "ventilation"), and the regional scale information in multiple regions (e.g. regions 150, 152, 154 shown in FIG. 14) of the lung a ventilation/perfusion measure is obtained throughout the lung, allowing for a regional comparison of ventilation/perfusion. This method therefore allows for the detection of heterogeneous ventilation/perfusion, a well known sign of ill lung health.

One method for evaluating the V/Q is a feeder based, tree based or anatomy based method. Regions in the lung are fed air and blood by paired airway and artery (a vein is also present). As such, the entire region of lung distal to a point 131 in an artery or airway (i.e. the portion of interest) is largely fed from that point. By selecting a measure of ventilation and perfusion associated with the airway and artery at that location an excellent measure of V/Q is obtained for the entire region distal to that location. The regional vessel calibre measurements described herein are an excellent surrogate for perfusion, and the motion measurements described above allow for measurement of the flow in an airway at the same location.

Alternatively, another method for evaluating the V/Q is a region based method. For any region of the lung (even a region that is not tree based or anatomically based—e.g. a cube of tissue) statistical approaches (as described above) can be taken as surrogates of ventilation and perfusion. There are also several ways to provide a measure of the ventilation. For example, the total expansion summed over every voxel in the region could be calculated, or modal or mean expansion in the region could be determined.

While the present invention has been discussed as utilising images acquired in the absence of contrast agent (which provides health benefits to the patient), it is envisaged that the technique could also be applied to images using contrast agent. In addition, while the invention is discussed in relation to the lungs, it is envisaged that the method could be applied to vessels in other parts of the body. For example, the method could be applied to other organs in the body, such as the brain, heart, liver and kidneys.

It is envisaged that the method of the present invention could be used as a surrogate measure for severity of PAH within the lung. It is also envisaged that, if narrowing of vessels is shown to correlate with artery pressure measured by right heart catheterisation, the method will also be able to predict pulmonary artery pressure. This would enable the non-invasive measurement of pulmonary artery pressure, which normally requires right heart catheterization, potentially eliminating the need for invasive pressure measurements in the diagnosis and management of patients with PAH. Furthermore, while the invention is discussed in relation to imaging humans, it is envisaged that the same method can be applied to animals, for example in pre-clinical trials.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™, Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal; Perl; PL/I; Prolog; Python; Rexx; SAS; Scheme; sed; Simula; Smalltalk; Snobol; SQL; Visual Basic; Visual C++; Linux and XML.) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g, a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internet working technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A method of scanning for vascular ill health, the method comprising:
    obtaining, at a processor, a scan data set from an in vivo scan comprising a vasculature tree, wherein the in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;
    extracting, by the processor, blood vessel location data and blood vessel size data from the scan data set, wherein extracting comprises:
        applying a multi-scale filter to the scan data set at each of a plurality of single scales to provide for each single scale, a single scale probability field;
        combining a plurality of the single scale probability fields to form an overall probability field and a scale field;
        performing vessel segmentation on the overall probability field to extract a segmented vasculature tree; and
        mapping the segmented vasculature tree to the scale field to quantify a geometry of the vasculature tree, wherein the geometry comprises blood vessel location data and blood vessel size data corresponding to diameter data;
    selecting, by the processor, a region in the extracted blood vessel location data;
    comparing, by the processor, the blood vessel size data in the selected region to blood vessel size data associated with blood vessel location data in a corresponding region of a normative data set; and determining vascular health based on the comparing.

2. The method of claim 1, wherein the normative data set is an average of multiple scans of healthy vasculature.

3. The method of claim 1, wherein the in vivo scan is one of a 2D in vivo scan or a 3D in vivo scan.

4. The method of claim 1, wherein the in vivo scan is converted to a visual image.

5. The method of claim 1, wherein the in vivo scan is an X-ray computer tomography (CT) scan.

6. The method of claim 1, wherein comparing, by the processor, the blood vessel size data in the selected region to blood vessel size data associated with blood vessel location data in a corresponding region of a normative data set comprises:

determining a statistical measure based on the blood vessel size data in the selected region;

determining a corresponding statistical measure based on the blood vessel size data in the corresponding region of the normative data set; and determining a difference between the statistical measure and the corresponding statistical measure.

7. The method of claim 6, wherein determining vascular health based on the comparing comprises:

responsive to the statistical measure being less than the corresponding statistical measure, determining a presence of vascular ill health.

8. The method of claim 6, wherein:

the blood vessel size data in the selected region is the blood vessel size data for an identified blood vessel in the selected region, and the blood vessel size data in the corresponding region of the normative data set is the blood vessel size data for a blood vessel in the normative data set that corresponds to the identified blood vessel in the selected region.

9. The method of claim 1, wherein comparing, by the processor, the blood vessel size data in the selected region to blood vessel size data associated with blood vessel location data in a corresponding region of a normative data set comprises:

determining a vascular size versus probability distribution for the selected region based on the blood vessel size data in the selected region;

identifying a primary peak and a secondary peak in the vascular size versus probability distribution for the selected region determining a corresponding vascular size versus probability distribution for the normative data set based on the blood vessel size data in the corresponding region of the normative data set;

identifying a normative primary peak and a normative secondary peak in the vascular size versus probability distribution for the normative data set; and determining a relationship between the primary peak and the secondary peak in the vascular size versus probability distribution for the selected region relative to the normative primary peak and the normative secondary peak in the vascular size versus probability distribution for the normative data set.

10. The method of claim 9, wherein the relationship is a difference between the primary peak and the normative primary peak and a difference between the secondary peak and the normative secondary peak, and determining vascular health based on the comparing comprises:

responsive to the primary peak and the secondary peak in the vascular size verses versus probability distribution for the selected region being greater than the normative primary peak and the normative secondary peak in the vascular size versus probability distribution for the normative data set, determining a presence of vascular ill health.

11. The method of claim 9, wherein the relationship is a difference between a ratio of the primary peak to the secondary peak and a ratio of the normative primary peak and the normative secondary peak, and determining vascular health based on the comparing comprises:

responsive to the ratio of the primary peak to the secondary peak being greater than the ratio of the normative primary peak and the normative secondary peak, determining a presence of vascular ill health.

12. The method of claim 1, wherein comparing, by the processor, the blood vessel size data in the selected region to blood vessel size data associated with blood vessel location data in a corresponding region of a normative data set comprises:

determining a first distribution of a vascular size versus generation number for the selected region based on the blood vessel size data in the selected region;

determining a corresponding second distribution of a vascular size versus generation number for the normative data set based on the blood vessel size data in the corresponding region of the normative data set; and determining a difference between the first distribution and the corresponding second distribution at all available generation numbers.

13. The method of claim 12, wherein determining vascular health based on the comparing comprises:

responsive to vascular size values of the first distribution being less than vascular size values of the corresponding second distribution for the normative data set, determining a presence of vascular ill health.

14. The method of claim 1, wherein comparing, by the processor, the blood vessel size data in the selected region to blood vessel size data associated with blood vessel location data in a corresponding region of a normative data set comprises:

determining a vascular size distribution for the selected region based on the blood vessel size data in the selected region;

determining a corresponding vascular size distribution for the normative data set based on the blood vessel size data in the corresponding region of the normative data set; and determining a difference between the respective distributions.

15. The method of claim 14, wherein:

each of the vascular size distribution for the selected region and corresponding vascular size distribution for the normative data set is a distribution of blood vessel volume versus blood vessel diameter; and determining vascular health based on the comparing comprises, responsive to the blood vessel volume of the vascular size distribution for the selected region being predominately less than the blood vessel volume of the corresponding vascular size distribution for the normative data set, determining a presence of vascular ill health.

16. The method of claim 14, wherein:

each of the vascular size distribution for the selected region and corresponding vascular size distribution for the normative data set is a distribution of a blood vessel length versus blood vessel cross-section area; and determining vascular health based on the comparing comprises responsive to blood vessel lengths of the vascular size distribution for the selected region being less evenly distributed than blood vessel lengths of the corresponding vascular size distribution for the normative data set, determining a presence of vascular ill health.

17. The method of claim 14, wherein:

each of the vascular size distribution for the selected region and corresponding vascular size distribution for the normative data set is a distribution of a blood vessel volume versus blood vessel cross-section area; and determining vascular health based on the comparing comprises, responsive to the blood vessel volume of the vascular size distribution for the selected region being predominately less than the blood vessel volume of the corresponding vascular size distribution for the normative data set, determining a presence of vascular ill health.

18. The method of claim 14, wherein:

each of the vascular size distribution for the selected region and corresponding vascular size distribution for the normative data set is a map of blood vessel size versus distance from a point in the vasculature tree; and determining vascular health based on the comparing comprises responsive to the map for the selected region having blood vessel sizes that are less than blood vessel sizes of the corresponding map for the normative data set, determining a presence of vascular ill health.

19. A method of scanning for lung ill health, the method comprising:

obtaining, at a processor, a scan data set from an in vivo scan comprising a vasculature tree, wherein the in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;

extracting, by the processor, blood vessel location data and blood vessel size data from the scan data set, wherein extracting comprises:

applying a multi-scale filter to the scan data set at each of a plurality of single scales to provide for each single scale, a single scale probability field;

combining a plurality of the single scale probability fields to form an overall probability field and a scale field;

performing vessel segmentation on the overall probability field to extract a segmented vasculature tree; and mapping the segmented vasculature tree to the scale field to quantify a geometry of the vasculature tree, wherein the geometry comprises blood vessel location data and blood vessel size data corresponding to diameter data;

selecting, by the processor, a first region and a second region in the extracted blood vessel location data;

comparing, by the processor, the blood vessel size data associated with the blood vessel location data in the first region to the blood vessel size data associated with the blood vessel location data in the second region; and determining vascular health based on the comparing.

20. The method of claim 19, wherein the lung ill health comprises one of pulmonary hypertension, pulmonary embolism, congestive heart failure, acute lung injury and lung cancer.

21. The method of claim 19, wherein the in vivo scan is converted to a visual image.

22. The method of claim 19, wherein the in vivo scan is an X-ray computer tomography (CT) scan.

23. A method of assessing efficacy of a lung disease treatment, the method comprising:

obtaining, at a processor, a pre-treatment scan data set from a pre-treatment in vivo scan comprising a vasculature tree, wherein the pre-treatment in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;

obtaining, at the processor, a post-treatment scan data set from a post-treatment in vivo scan comprising the vasculature tree, wherein the post-treatment in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;

extracting, by the processor, blood vessel location data and blood vessel size data from the pre-treatment scan data set by:

applying a multi-scale filter to the pre-treatment scan data set at each of a plurality of single scales to provide for each single scale, a single scale probability field;

combining a plurality of the single scale probability fields to form an overall probability field and a scale field;

performing vessel segmentation on the overall probability field to extract a segmented vasculature tree; and mapping the segmented vasculature tree to the scale field to quantify a geometry of the vasculature tree, wherein the geometry comprises blood vessel location data and blood vessel size data corresponding to diameter data; and extracting, by the processor, blood vessel location data and blood vessel size data from the post-treatment scan data set by:

applying the multi-scale filter to the post-treatment scan data set at each of a plurality of single scales to provide for each single scale, a single scale probability field;

combining a plurality of the single scale probability fields to form an overall probability field and a scale field;

performing vessel segmentation on the overall probability field to extract a segmented vasculature tree; and mapping the segmented vasculature tree to the scale field to quantify a geometry of the vasculature tree, wherein the geometry comprises blood vessel location data and blood vessel size data corresponding to diameter data;

selecting, by the processor, a region in the extracted blood vessel location data from either the pre-treatment scan data set or the post-treatment scan data set;

comparing, by the processor, the blood vessel size data associated with the blood vessel location data in the selected region to the blood vessel size data associated with the blood vessel location data of a corresponding region in the other scan data set; and
assessing the efficacy of the lung disease treatment based on the comparing.

24. The method of claim 23, wherein the lung disease treatment comprises application of a pharmaceutical active or immuno-therapeutic agent.

25. The method of claim 23, wherein:
the pre-treatment in vivo scan is an X-ray computer tomography (CT) scan, and
the post-treatment in vivo scan is an X-ray computer tomography (CT) scan.

26. A non-transitory computer readable storage medium having a computer program stored therein, wherein the program, when executed by a processor of a computer, causes the computer to:
obtain a scan data set from an in vivo scan comprising a vasculature tree, wherein the in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;
extract blood vessel location data and blood vessel size data from the scan data set by causing the computer to:
apply a multi-scale filter to the scan data set at each of a plurality of single scales to provide for each single scale, a single scale probability field;
combine a plurality of the single scale probability fields to form an overall probability field and a scale field;
perform vessel segmentation on the overall probability field to extract a segmented vasculature tree; and
map the segmented vasculature tree to the scale field to quantify a geometry of the vasculature tree, wherein the geometry comprises blood vessel location data and blood vessel size data corresponding to diameter data;
select a region in the extracted blood vessel location data;
compare the blood vessel size data in the selected region to the blood vessel size data associated with blood vessel location data in a corresponding region of a normative data set; and
determine vascular health based on the comparison.

27. A non-transitory computer readable storage medium having a computer program stored, wherein the program, when executed by a processor of a computer, causes the computer:
obtain a scan data set from an in vivo scan comprising a vasculature tree, wherein the in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;
extract blood vessel location data and blood vessel size data from the scan data set by causing the computer to:
apply a multi-scale filter to the scan data set at each of a plurality of single scales to provide for each single scale, a single scale probability field;
combine a plurality of the single scale probability fields to form an overall probability field and a scale field;
perform vessel segmentation on the overall probability field to extract a segmented vasculature tree; and
map the segmented vasculature tree to the scale field to quantify a geometry of the vasculature tree, wherein the geometry comprises blood vessel location data and blood vessel size data corresponding to diameter data;
select a first region and a second region in the extracted blood vessel location data;
compare the blood vessel size data associated with the blood vessel location data in the first region to the blood vessel size data associated with the blood vessel location data in the second region; and
determine vascular health based on the comparison.

28. A non-transitory computer readable storage medium having a computer program stored, wherein the program, when executed by a processor of a computer, causes the computer:
obtain a pre-treatment scan data set from a pre-treatment in vivo scan comprising a vasculature tree, wherein the pre-treatment in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;
obtain a post-treatment scan data set from a post-treatment in vivo scan comprising the vasculature tree, wherein the post-treatment in vivo scan is acquired in an absence of a contrast agent and is one of a fluoroscopy scan, an X-ray computer tomography (CT) scan, a four-dimensional CT (4D-CT) scan, a magnetic resonance imaging (MRI) scan, and an ultrasound scan;
extract blood vessel location data and blood vessel size data from the pre-treatment scan data set by causing the computer to:
apply a multi-scale filter to the pre-treatment scan data set at each of a plurality of single scales to provide for each single scale, a single scale probability field;
combine a plurality of the single scale probability fields to form an overall probability field and a scale field;
perform vessel segmentation on the overall probability field to extract a segmented vasculature tree; and
map the segmented vasculature tree to the scale field to quantify a geometry of the vasculature tree, wherein the geometry comprises blood vessel location data and blood vessel size data corresponding to diameter data; and
extract blood vessel location data and blood vessel size data from the post-treatment scan data set by causing the computer to:
apply the multi-scale filter to the post-treatment scan data set at each of a plurality of single scales to provide for each single scale, a single scale probability field;
combine a plurality of the single scale probability fields to form an overall probability field and a scale field;
perform vessel segmentation on the overall probability field to extract a segmented vasculature tree; and
map the segmented vasculature tree to the scale field to quantify a geometry of the vasculature tree, wherein the geometry comprises blood vessel location data and blood vessel size data corresponding to diameter data;
select a region in the extracted blood vessel location data from either the pre-treatment scan data set or post-treatment scan data set;
compare the blood vessel size data associated with the blood vessel location data in the selected region to the blood vessel size data associated with the blood vessel location data of a corresponding region in the other scan data set; and assess an efficacy of a lung disease treatment based on the comparison.

* * * * *